(12) United States Patent
Liang (10) Patent No.: US 7,441,901 B2
(45) Date of Patent: Oct. 28, 2008

(54) MULTITASK VISION ARCHITECTURE FOR REFRACTIVE VISION CORRECTIONS

(75) Inventor: Junzhong Liang, Fremont, CA (US)

(73) Assignee: Advanced Vision Engineering, Inc., Fremont, CA (US)

( * ) Notice: Subject to any disclaimer, the term of this patent is extended or adjusted under 35 U.S.C. 154(b) by 226 days.

(21) Appl. No.: 11/432,274

(22) Filed: May 10, 2006

(65) Prior Publication Data

US 2006/0279700 A1 Dec. 14, 2006

Related U.S. Application Data

(60) Provisional application No. 60/690,602, filed on Jun. 14, 2005.

(51) Int. Cl.
*A61B 3/00* (2006.01)

(52) U.S. Cl. ...................................... 351/246; 351/205

(58) Field of Classification Search ................. 351/246, 351/247, 200, 205, 221, 211
See application file for complete search history.

(56) References Cited

U.S. PATENT DOCUMENTS 6,948,818 B2 * 9/2005 Williams et al. ............ 351/211

* cited by examiner

*Primary Examiner*—Hung Dang (57) ABSTRACT

A multitask vision architecture is constructed based on multitask vision-metrics derived from wave aberration of the eye. The multitask vision metrics include at least one of the followings: vision clarity of eye that measures optical quality of an eye against those in a cohort of eyes with normal acuity, aberration-induced vision symptoms, retinal image quality for best vision and night vision, and retinal image quality for a range of focus depth. The multitask vision architectures is applied for determining a wavefront shape for an optimized vision correction, for specifying excessive aberrations in an eye, and for specifying quality of a vision product.

32 Claims, 6 Drawing Sheets

6 meters away from the eye

Fig.1a

Fig.1b 3 meters away from the eye

Fig.1c

Fig.1d 30 meters away from the eye

MULTITASK VISION ARCHITECTURE FOR REFRACTIVE VISION CORRECTIONS

CROSS-REFERENCES TO RELATED INVENTIONS

The present invention claims priority to the provisional U.S. patent application 60/690,602, titled "Multitask vision metrics and multitask architecture for refractive vision corrections" filed Jun. 14, 2005 by Liang. The present invention is related to U.S. patent application Ser. No. 11/371,288, filed Mar. 8, 2006, for "Algorithms and methods for determining aberration-induced vision symptoms in the eye from wave aberration" by Liang, and U.S. patent application Ser. No. 11/370,745, filed Mar. 8, 2006, for "Methods for specifying image quality of human eyes from wave aberration" by Liang. The disclosures of these related applications are incorporated herein by reference.

TECHNICAL FIELD

This application relates to systems and methods for refractive vision corrections, in particular, for designing, specifying, and evaluating refractive vision corrections.

BACKGROUND

Wavefront-guide technology, or customized vision correction, is becoming a new frontier for vision and ophthalmology because it offers the capability to manipulate high-order aberrations in the eye. There are fundamentally two kinds of wavefront customizations: supernormal vision corrections that allow the correction of high-order aberrations in an eye and presbyopic corrections that increase focus depth of an eye by introducing certain high-order aberrations.

Supernormal vision corrections were first obtained in laboratories using a technology called adaptive optics, as disclosed in "Supernormal vision and high resolution retinal imaging through adaptive optics," J. Opt. Soc. Am. A, vol. 14, pp2884-2892 by Liang, Williams and Miller in 1997, and in U.S. Pat. No. 5,777,719, issued Jul. 7, 1998 by Williams and Liang. Since the first demonstration of supernormal vision with adaptive optics, extensive efforts have been made recently in the filed of laser vision correction as described in "Aberration-Free Refractive Surgeries," Springer-Verlag, 2003, Bille et al ed., and in "Wavefront Customized Visual Correction: The Quest for Super Vision II,", Slack Inc, 2004, Krueger et al ed.

Figure 1A:
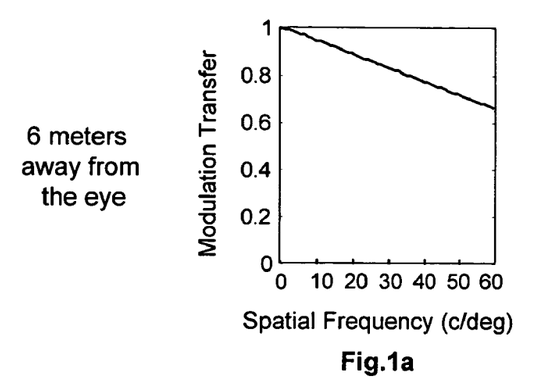
FIG. 1 shows Modulation-Transfer Functions and simulated retinal images for an aberration-free eye in three viewing distances. The aberration-free eye has a pupil size of 6.5 mm and is refracted to have the best focus at a view distance of 6 meters away from the eye.
Figure 1B:
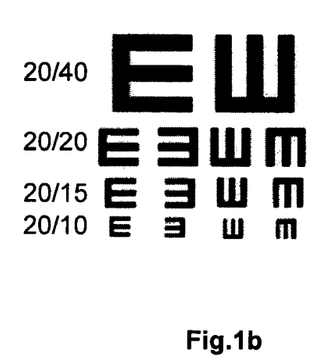
Figure 1C:
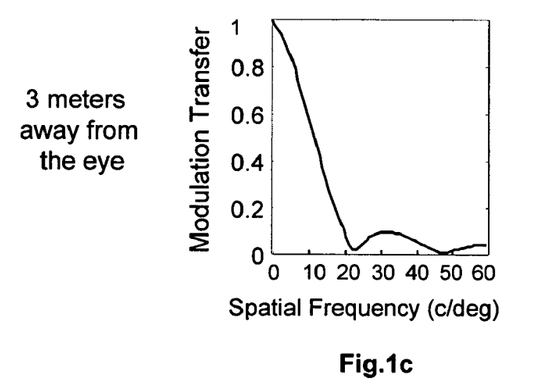
Figure 1D:
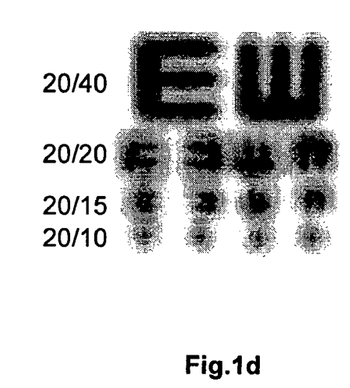
Figure 1E:
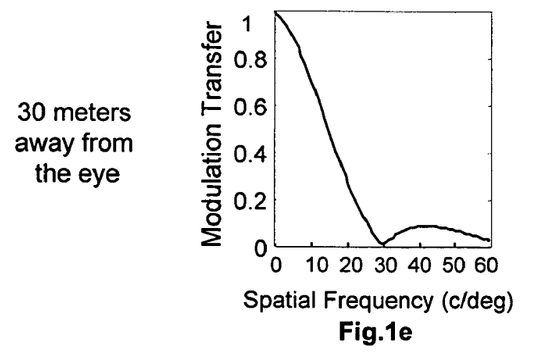
Figure 1F:
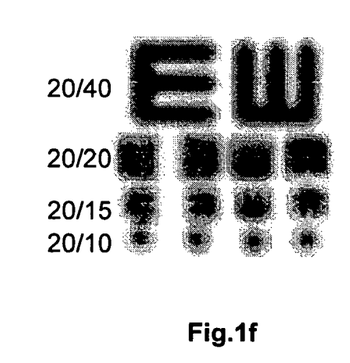

An ultimate goal for a supernormal vision correction has been to create an aberration-free eye. FIG. 1 shows the Modulation-Transfer Functions (MTF) and simulated retinal images of an acuity chart for an aberration-free eye in three viewing distances. FIG. 1a and FIG. 1b show a Modulation-Transfer Function (MTF) and simulated retinal images of an acuity chart for an aberration-free eye at the best focus. We assume the aberration-free eye is refracted to have the best focus 6 meters away from the eye, matching to the situation in a conventional subjective refraction. Because human eyes must function for a range of focus depth, we also show MTFs and retinal images of the same aberration-free eye at 3 meters (a focus shift of 0.17 Dioptors) in FIG. 1c and FIG. 1d, and at 30 meters (a focus shift of 0.13 Dioptors) in FIG. 1e and FIG. 1f. Two important aspects are clearly seen for the aberration-free eye. First, the aberration-free eye has extremely clear vision at the best focus, shown in the retinal images as well as in MTF at the high frequency around 60 c/deg. Second, the aberration-free eye is extremely sensitive to a focus offset, even as small as 0.1 Dioptors.

One should re-consider the creation of aberration-free eyes for at least two reasons. First, an aberration-free eye can only see clearly at the exact focus position; and a slight shift of focus (about 0.1 Dioptors) will make vision of the eye totally blurred. Second, at the exact focus position with superior clarity, the aberration-free eye won't be good for all vision tasks, in particular for high frequency structures. Improved image quality with an aberration-free optics could cause mismatches between aberration-free optics of the eye and the retinal sampling by photoreceptors. It is possible that aliasing may happen for high-frequency features and distort vision as described in "Aliasing in human foveal vision" Vision Research, vol. 25, pp195-205 by D R Williams in 1985.

Wavefront customizations also include presbyopic treatments for elderly eyes. Certain high-order aberrations such as spherical aberration can be introduced into elderly eyes for increased focus depth. However, increasing focus depth must come at a cost of reduced image quality. If not controlled properly, the introduced high-order aberrations will not only reduced image contrast, but also cause unwanted vision symptoms such as glare, halo, and starburst.

Wavefront technology not only offers advantages for altering high-order aberrations in the eye, but also poses challenges to design, evaluation and specification of wavefront-guided vision correction. Improper wavefront corrections can cause harms to vision rather than improve vision quality.

In light of the forgoing, it is readily apparent that a need exists in the art to provide a comprehensive vision architectures for designing, specifying and diagnosing wavefront-guided vision corrections. The comprehensive architecture must contain a more reasonable performance target than an aberration-free eye, enable to predict vision quality from wave aberration in the eye, and include features to prevent vision symptoms such as glare, halo, starburst, and ghost images.

An additional need also exists in the art to provide methods to specify wavefront-guided vision correction beyond visual acuity, because good acuity is a necessary but not a sufficient condition for excellent vision. With introduction of new products based on new procedures, new materials, and new correction forms, specifying vision quality beyond visual acuity is necessary to prevent potentially inferior products with night vision symptoms, insufficient vision clarity and insufficient focus depth.

SUMMARY

The present invention generally provides a multitask vision architecture that is constructed based on multitask vision-metrics derived from wave aberration of the eye. The multitask vision metrics include at least one of the followings: vision clarity of eye that ranks optical quality of an eye against those in a cohort of eyes with normal acuity, aberration-induced vision symptoms, retinal image quality for best vision and night vision, and retinal image quality for a range of focus depth. The multitask vision architectures is a comprehensive platform for determining a wavefront shape for an optimized vision correction, for specifying excessive aberrations in the eye, and for specifying quality of a vision products.

Implementations of the method may include one or more of the following. In one aspect, the present invention relates to a method for determining an optimized wavefront correction, the method comprising: obtaining at least one wave aberration of an eye; selecting at least one performance target based on optical quality of a cohort of eyes with normal visual acuity; determining a post-correctional wavefront by altering aberrations in the eye to meet the selected performance target; determining a wavefront shape for an optimized wavefront correction as the difference between the obtained wave aberration of the eye and the determined post-correctional wavefront that meet the selected performance target.

In another aspect, the invention method for determining an optimized wavefront correction further comprises wavefront optimization to eliminate night vision symptoms as well as for improved focus depth.

In an additional aspect, a method for specifying quality of a vision product, the method comprising: obtaining at least one wave aberration of an eye with a vision product; calculating at least one image quality parameter from the wave aberration; specifying quality of a vision product as a relative score based on the calculated image quality parameter and those same parameters of a cohort of eyes with normal visual acuity.

In yet an additional aspect, a method for specifying quality of a correction lens, the method comprising: obtaining at least one wave aberration of an eye; obtaining at least one wavefront measurement of an correction lens from a wavefront lensometer; determining a post-correctional wavefront by combining the obtained wave aberration of the eye and the measured wavefront of the correction lens; calculating at least one image quality parameter from the post-correctional wavefront; specifying quality of a correction lens as a relative score based on optical quality of a cohort of eyes with normal visual acuity.

Embodiments may include one or more of the following advantages. First, the invention method provides a multitask architecture for refractive vision corrections. It enables to optimize vision correction for vision clarity beyond visual acuity as well as for improved night vision performance. It also allows performance-based vision screening for uncorrected eyes, vision diagnosis of symptomatic eyes, and comprehensive specification of post-correction eyes. Second, the invention method is based on optical quality of normal human eyes. Optimized wavefront corrections will not cause mismatches between the improved optical quality and the retinal performances. Third, the invention methods provide improved, performance-based specifications for vision correction beyond conventional visual acuity.

The details of one or more embodiments are set forth in the accompanying drawings and in the description below. Other features, objects, and advantages of the invention will become apparent from the description and drawings, and from the claims.

DRAWING DESCRIPTIONS

FIG. 2 shows multitask vision-metrics on which a multitask vision architecture is constructed.

DETAILED DESCRIPTION OF THE INVENTION

New vision-metrics were disclosed in the following U.S. patent applications, the entire disclosures of which are hereby incorporated by reference: U.S. patent application Ser. No. 11/371,288, filed Mar. 8, 2006, for "Algorithms and methods for determining aberration-induced vision symptoms in the eye from wave aberration"; and U.S. patent application Ser. No. 11/370,745, filed Mar. 8, 2006, for "Methods for specifying image quality of human eyes from wave aberration."

The disclosed new vision-metrics were designed to overcome limitations of conventional visual acuity. In one aspect, they provide a comprehensive, multitask specification of retinal image quality including visual clarity and aberration-induced vision symptoms. In another aspect, vision clarity is a relative score system designed for ranking vision quality of eyes with same acuity into a number of grades. In yet another aspect, all the disclosed vision-metrics can be derived directly from wave aberration in the eye. Vision-metrics with these distinct advantages open the door for a comprehensive vision architecture.

Figure 2A:
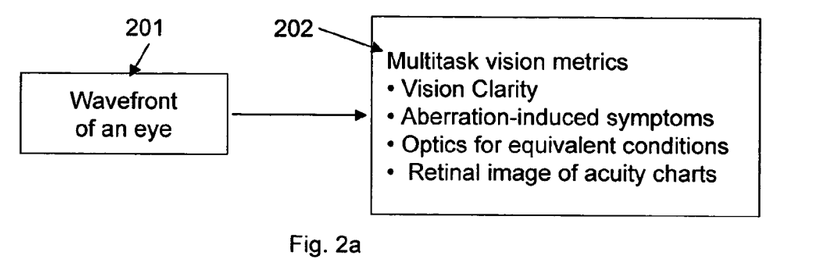
FIG. 2a shows multitask vision metrics of an eye derived from the wavefront in the eye, including vision clarity, aberration-induced symptoms, retinal images of resolution charts, and optics for three equivalent pupil conditions at variable pupil sizes.

The present invention describes a multitask vision architecture that is constructed based on multitask vision-metrics derived from wave aberration as shown in FIG. 2a, including vision clarity, aberration-induced vision symptoms, optics for equivalent conditions and retinal image of acuity charts.

Figure 2B:
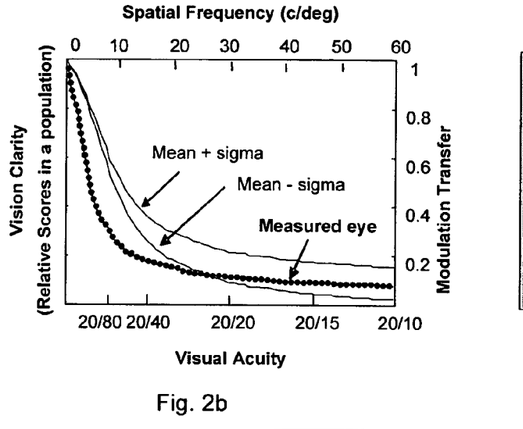
FIG. 2b shows vision clarity in a statistical 3-score MTF system, disclosed in U.S. patent application Ser. No. 11/370,745.

Vision Clarity (VC), disclosed in U.S. patent application Ser. No. 11/370,745, generally provides a relative score system for ranking modulation-transfer function (MTF) of an eye with normal visual acuity into a number of grades. It is derived from wave aberration of an eye by obtaining at least one wave aberration of a tested eye, calculating at least one modulation transfer function from the obtained wave aberration, determining vision clarity of the eye using a relative score system derived from the calculated modulation transfer function of the tested eye and a set of modulation transfer functions from a cohort of eyes with normal visual acuity. Referring to FIG. 2b in one embodiment, vision clarity is categorized by a statistical 3-score system: "normal" if MTF of an eye is within one standard deviation of the mean MTF of a cohort of eyes with normal acuity (between mean+sigma and mean−sigma), "better than normal" if MTF of an eye is above the mean plus one standard deviation (above mean+sigma), "worse than normal" if MTF of an eye is below the mean minus one standard deviation (below mean−sigma). An alternative representation of vision clarity with more grades is to rank vision clarity in percentiles. Vision clarity effectively separates good, normal, and bad eyes from all eyes with same visual acuity.

Figure 2C:
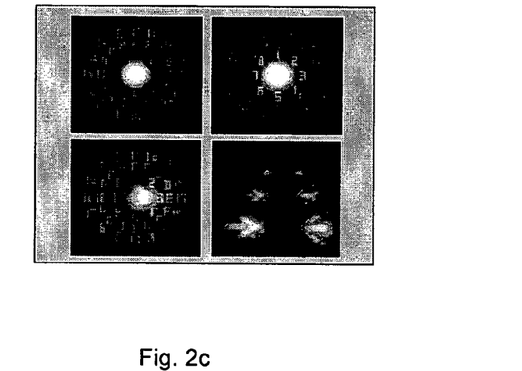
FIG. 2c shows aberration-induced symptoms including halo (top right), glare (bottom left) and starburst (bottom right), disclosed in U.S. patent application Ser. No. 11/371,288.

The method for aberration-induced vision symptoms, disclosed in U.S. patent application Ser. No. 11/371,288, provides the first known mean for displaying and specifying vision symptoms. It is obtained by measuring at least one wave aberration of an eye, calculating at least one point-spread function from the wave aberration, convolving the point-spread function of eye with at least one specially designed image for night vision diagnosis, determining at least one aberration-induced vision symptom of the tested eye from the convolved images. FIG. 2c shows aberration-induced halo (top right), glare (bottom left) and starburst (bottom right). The method of aberration-induced symptoms effectively links aberrations in the eye to specific vision symptoms for the first time. It can be used to identify vision symptoms for refractive vision corrections.

Figure 2D:
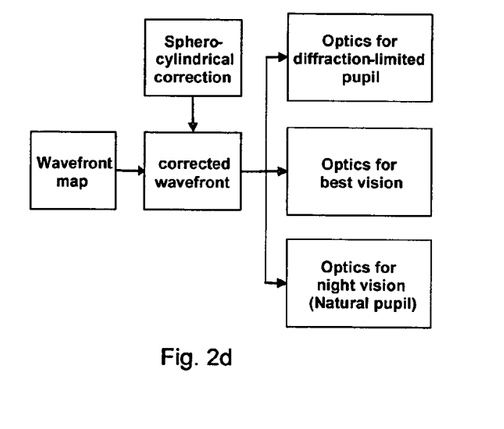
FIG. 2d shows optics of an eye specified in three equivalent conditions at variable pupil sizes, disclosed in U.S. patent application Ser. No. 11/370,745.

Natural pupil of an eye is known to vary greatly depending on surrounding light conditions. It can be as small as 1.5 mm in daylight and as large as 8 mm at night. Engineering the eye must deal with optics at all possible view conditions. Referring to FIG. 2d, vision quality is specified in three equivalent conditions at variable pupil sizes, disclosed in U.S. patent application Ser. No. 11/370,745. Differing from traditionally comparing image quality at identical pupil sizes, we specify three equivalent conditions to fully describe image quality of eye at all pupil sizes. They include optics for diffraction-limited pupil, optics for best vision, and optics for night vision.

Figure 2E:
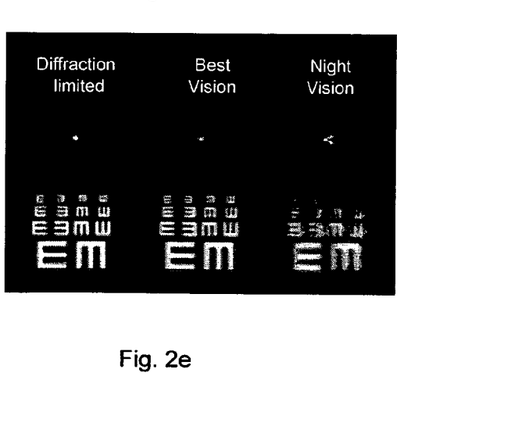
FIG. 2e shows an example of retinal images of an eye in the three equivalent pupil conditions.

As an example, FIG. 2e shows retinal images of an acuity chart for an eye in the three pupil conditions. They were obtained by measuring at least one wave aberration of an eye, calculating point-spread functions of the eye (top) for diffraction-limited pupil, for best vision and for night vision from the wave aberration, convolving the point-spread functions of eye with an acuity chart. Optics-limited resolution in the eye can be assessed from the calculated retinal images (bottom).

Multitask vision-metrics in FIG. 2 solves the missing links between wavefront at the corneal plane and the retinal image quality at the retinal plane. The parameters in vision-metrics are objective, and can be derived directly from the wave aberrations. They form the base for multitask vision architecture of the present invention.

Figure 3:
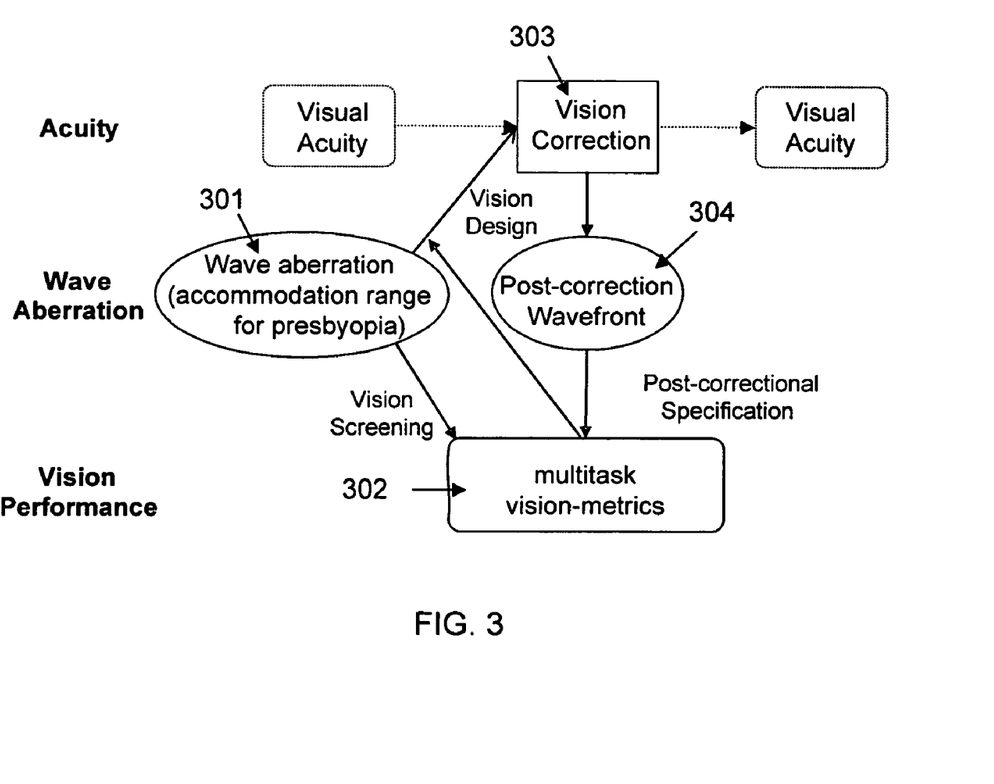
FIG. 3 shows a block diagram of multitask vision architecture in accordance with the present invention.

FIG. 3 shows a block diagram of the multitask vision architecture based on multitask vision-metrics. In one aspect, wave aberration of an eye before a vision correction 301 is measured with a wavefront sensor, and vision performances of the eye are derived according to multitask vision-metrics 302 for vision screening before a vision correction. In another aspect, an optimized wavefront shape 303 is determined through a recursive optimization based on a multitask vision-metrics 302. The optimized wavefront is then applied to the eye for a wavefront refractive correction 303. In an additional aspect, wave aberration of an eye after a vision correction 304 is measured with a wavefront sensor, and vision performances of the eye are derived for post-correctional specification 302.

Figure 4:
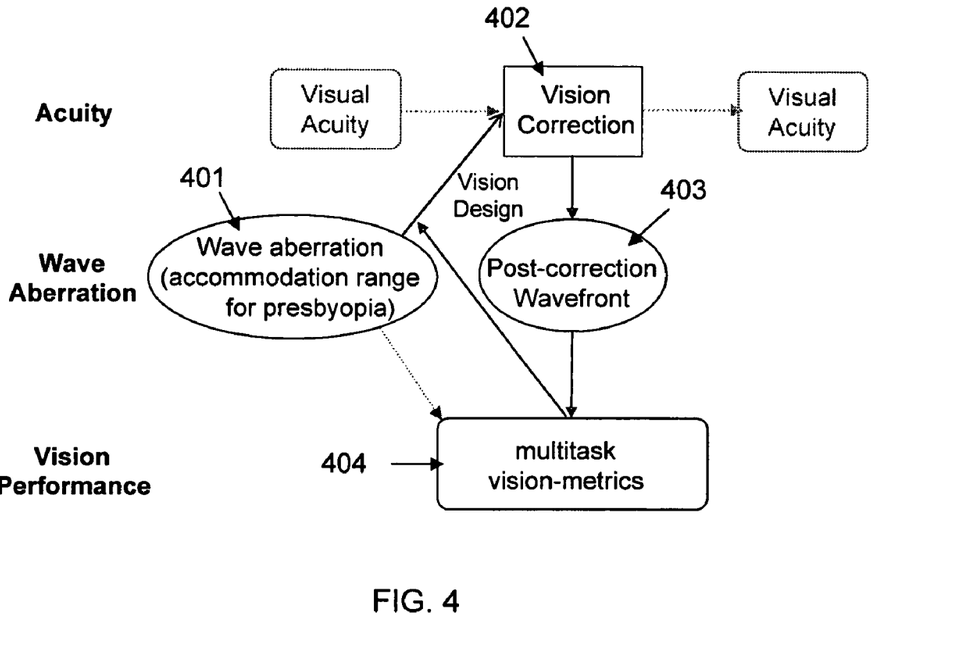
FIG. 4 shows a block diagram of vision optimization for a wavefront-guided vision correction based on multitask vision-metrics in accordance with the present invention.

In one preferred embodiment, optimized wavefront shapes for wavefront-guided vision corrections are determined according to the block diagram shown in FIG. 4. First, parameters of a treated eye's optics before a vision correction 401 are measured. They may include eye's wave aberration, pupil sizes, and the accommodation range for a treatment of hyperopia. Second, an initial wavefront shape for a vision correction 402 is assigned based on the characteristics as well as limitations of a specific procedure of vision correction.

Third, multitask vision-metrics 404 after the designed correction is derived from the post-correctional wavefront in the eye 403. The post-correctional wavefront 403 is the difference between the original wave aberration of the eye 401 and the correction wavefront shape for a vision correction 402. For treatments of presbyopia, vision-metrics should be calculated for a range of focus depth. Fourth, the simulated post-op vision-metrics 404 are evaluated against certain design criteria. Fifth, a revised post-operative wave aberration is derived by applying a new wavefront shape for a vision correction 402 to the pre-op wave aberration for a further optimization. Sixth, repeating step 3 through step 5 until an optimized wavefront shape for a vision correction 402 is obtained and the post-correctional vision-metrics meets the design criteria.

Design criteria in wavefront optimization may differ depending on the specific treatments. For treatments of young eyes with sufficient accommodation, wavefront-guided treatments should target a post-correctional performance at or above 50 percentile for vision clarity. For the treatment of presbyopia, wavefront-guided treatment should target a post-correctional performance at or above 15 percentile rank for vision clarity and for a range of focus depth.

Figure 5:
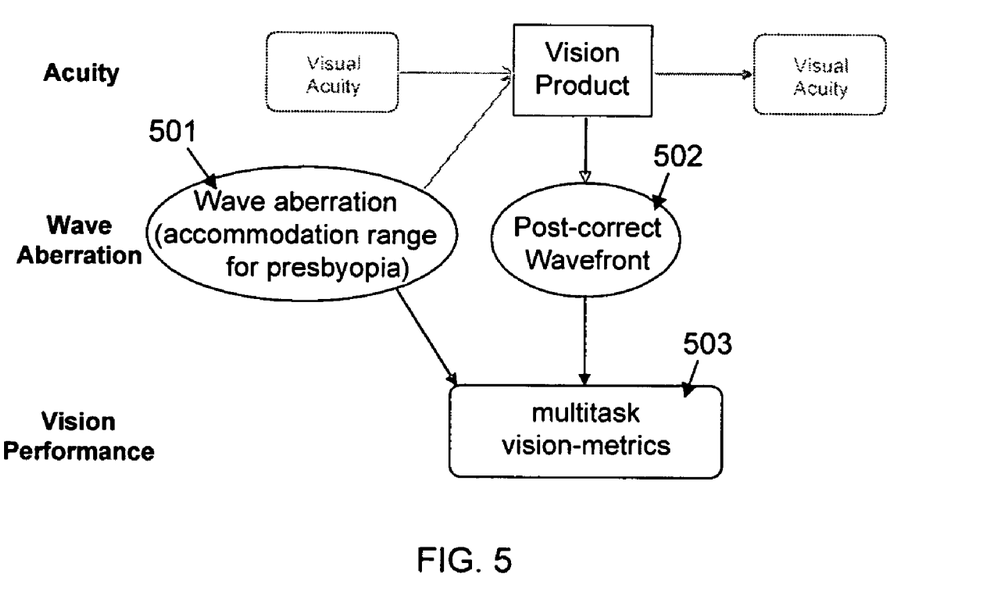
FIG. 5 shows a block diagram of specification of vision products using multitask vision-metrics in accordance with the present invention.

In another embodiment, multitask vision-metrics are used for comprehensive specifications of a vision correction as shown in FIG. 5. First, wave aberration of an eye before a vision correction 501 and wave aberration of an eye after a vision correction 502 are acquired. For the assessments of presbyopia, accommodation range of the eye should also be measured. Second, at least one of image performance parameters 503 is derived from the acquired wavefront of the eye before and after the vision correction. Third, vision of the corrected eye is specified according to the calculated vision-metrics of the eye including night vision symptoms and vision clarity.

Vision specifications based on multitask vision-metrics overcome limitations of visual acuity, and can have significant impacts on vision care. First, the new vision specifications of aberration-induced symptoms and vision clarity can be easily obtained in clinical settings in a conventional wavefront measurement. Second, new vision standard can be established base on the multitask vision-metrics to prevent inferior products entering into vision practices. Third, additional information based on multitask vision metrics can be used to promote superior vision products.

Figure 6:
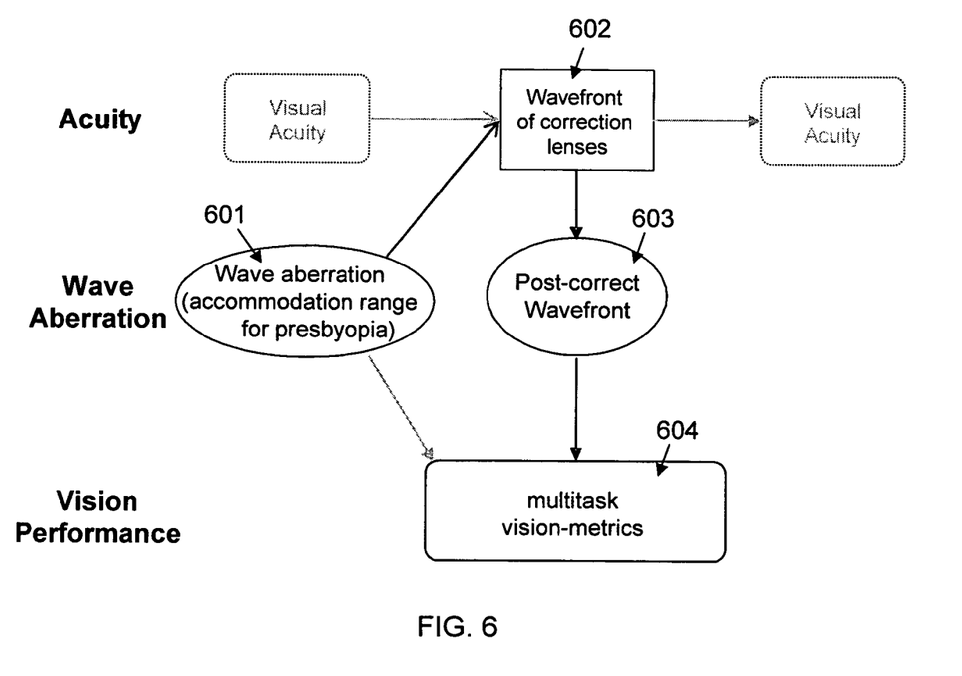
FIG. 6 shows a block diagram for specifying correction lenses using multitask vision metrics in accordance with the present invention.

In yet another embodiment, correction lenses are specified with multitask vision-metrics. Spectacles, contact lenses, Phakic intro-ocular lenses, and intro-ocular lenses are used for the corrections of nearsightedness, farsightedness, presbyopia. Conventional lenses are often characterized by spherical and cylindrical power only. With introduction of new wavefront-guided lenses, conventional specifications of lenses using spherical and cylindrical powers are no longer sufficient. FIG. 6 shows a block diagram for specifying lenses with multitask vision-metrics. First, wave aberration as well as pupil size of the eye before vision correction 601 are measured. Second, correction lenses 602 are measured with a wavefront lensometer for all aberrations in the correction lenses. Third, wave aberration of the eye 603 with the correction lens is derived by combining the wave aberration of the eye and the aberrations of the correction lens. Third, multitask vision-metrics 604 for the eye with the correction lenses 602 are calculated from the wavefront of the eye for the specification of vision with wavefront-guided lenses.

A number of embodiments have been described. Nevertheless, it will be understood that various modifications may be made without departing from the spirit and scope of the invention. For example, advantageous results still could be achieved if steps of the disclosed techniques were performed in a different order and/or if components in the disclosed systems were combined in a different manner and/or replaced or supplemented by other components. Accordingly, other embodiments are within the scope of the following claims.

What is claimed is:

1. A method for determining an optimized wavefront correction, the method comprising:
   obtaining at least one wave aberration of an eye;
   selecting at least one performance target based on optical quality of a cohort of eyes with normal visual acuity;
   determining a post-correctional wavefront by altering aberrations in the eye to meet the selected performance target;
   determining an optimized wavefront correction from the difference between the obtained wave aberration of the eye and the determined post-correctional wavefront that meets the selected performance target.

2. The method of claim 1, wherein obtaining at least one wave aberration of an eye comprises measuring at least one wave aberration of an eye with a wavefront aberrometer, including a Hartmann-Shack sensor based-aberrometer.

3. The method of claim 1, wherein the selected performance target relates to a Modulation-Transfer Function (MTF) of an eye for at least one spatial frequency.

4. The method of claim 3, wherein the selected performance target is a Modulation-Transfer Function (MTF) of at least one real eye that is ranked above 98 percentile in MTFs of a cohort of eyes with normal acuity.

5. The method of claim 3, wherein the selected performance target is a relative Modulation-Transfer Function (MTF) score at or above 50 percentile rank in MTFs of a cohort of eyes with normal acuity.

6. The method of claim 3, wherein the selected performance target is a relative Modulation-Transfer Function (MTF) score at about 15 percentile rank in a cohort of eyes with normal acuity.

7. The method of claim 1, wherein determining a post-correctional wavefront by altering aberrations in the eye to meet the selected performance target comprises:
   changing certain aberrations in the eye;
   obtaining a residual wavefront from the difference between the wave aberration of the eye and the changed certain aberrations in the eye;
   calculating at least one image performance parameter from the residual wavefront and comparing it against the selected performance target;
   determining a post-correctional wavefront in a recursive process until the selected performance target is reached.

8. The method of claim 7, further includes evaluation of retinal images with the determined post-correctional wavefront comprising:
   calculating at least one point-spread function from the post-correctional wavefront;
   calculating at least one retinal image by convolving the point-spread function of eye with at least one optical object for vision evaluation;
   accepting or rejecting the optimized wavefront based on the calculated retinal image.

9. The method of claim 8, wherein the optical object for vision evaluation is a resolution chart for acuity tests.

10. The method of claim 8, wherein the optical object for vision evaluation is a specially designed object for diagnosing vision symptoms, including aberration-induced glare, halo, ghost image, and starburst.

11. The method of claim 7, further comprises evaluation of vision for a plurality of pupil sizes.

12. The method of claim 7, further comprises evaluation of vision for a plurality of focus depth with the determined post-correctional wavefront.

13. The method of claim 1, further includes a laser vision correction procedure based on the determined wavefront shape for an optimized correction comprising:
   a processor for generating an ablation pattern of laser energy for ablation of a corneal tissue of the eye so as to achieve a wavefront-guided vision correction, the ablation pattern based at least in part on the determined wavefront shape for an optimized correction; and
   a laser system for directing laser energy onto the corneal tissue of the eye to achieve the generated ablation pattern.

14. The method of claim 1, further includes a system for producing a wavefront-guided contact lenses or intro-ocular lens, based at least in part on the determined wavefront shape for an optimized correction.

15. The method of claim 1, further includes a system for producing a wavefront-guided spectacles, based at least in part on the determined wavefront shape for an optimized correction.

16. The method of claim 1, wherein determining a post-correctional wavefront by altering aberrations in the eye to meet the selected performance target is a recursive process comprising:
   reducing a portion of aberrations in the wave aberration of the eye;
   obtaining a residual wavefront by the difference between the wave aberration of the eye and the reduced aberrations;
   calculating an image performance parameter from the obtained residual wavefront and comparing it against the selected performance target;
   determining a post-correctional wavefront by reducing more aberrations in the eye until the selected performance target is met.

17. The method of claim 1, further includes specifying excessive aberrations of an eye from the difference between the obtained wave aberration of the eye and the determined post-correctional wavefront.

18. The method of claim 17, wherein the selected performance target is a Modulation-Transfer Function (MTF) of an eye for at least one spatial frequency.

19. The method of claim 17, wherein the selected performance target is a Modulation-Transfer Function (MTF) of at least one real eye that is ranked above 98 percentile in MTFs of a cohort of eyes with normal acuity.

20. The method of claim 17, wherein the selected performance target is a relative Modulation-Transfer Function (MTF) score at or above 50 percentile rank in MTFs of a cohort of eyes with normal acuity.

21. A method for specifying quality of a vision product including lenses and refractive surgeries, the method comprising:
   obtaining at least one wave aberration of an eye with a vision product;
   calculating at least one image quality parameter from the obtained wave aberration;
   specifying quality of a vision product by a relative scare based on the calculated image quality parameter from the obtained wave aberration of the eye and the same parameter obtained from a cohort of eyes with normal visual acuity.

22. The method of claim 21, wherein obtaining at least one wave aberration of an eye after a vision correction comprises measuring at least one wave aberration of an eye with a wavefront aberrometer, including a Hartmann-Shack sensor based-aberrometer.

23. The method of claim 21. wherein the calculated image performance parameter is a modulation-transfer function (MTF) of the eye for at least one spatial frequency.

24. The method of claim 23, wherein the specified quality of a vision product is represented by a numerical number including a percentile rank by ranking the calculated MTF of the tested eye against those MTFs of a cohort of eyes with normal acuity.

25. The method of claim 21, wherein the calculated image quality parameter is a Strehl Ratio, or a volume under a 2-dimensional MTF of the eye up to a spatial frequency about 60 cycle/deg.

26. The method of claim 21, further includes a vision screening comprises:
    measuring at least one wave aberrations of the eye without using a vision product;
    calculating at least one image quality parameter from the wave aberration without the vision product;
    screening vision quality of the eye in a relative score by ranking the calculated image quality parameter from the eye against those from a cohort of eyes with normal visual acuity.

27. The method of claim 21, further includes specification of quality of a vision product in a plurality of pupil sizes.

28. A method for specifying quality of a correction lens, the method comprising:
    obtaining at least one wave aberration of an eye;
    measuring at least one wavefront of an correction lens from a wavefront lensometer;
    determining a post-correctional wavefront by combining the obtained wave aberration of the eye and the measured wavefront of the correction lens;
    calculating at least one image quality parameter from the post-correctional wavefront;
    specifying quality of a correction lens in a relative score based on optical quality of a cohort of eyes with normal visual acuity.

29. The method of claim 28, wherein the calculated image performance parameter is a modulation-transfer function (MTF) of the eye for at least one spatial frequency.

30. The method of claim 28, wherein specifying the image performance parameter in a relative score based on optical quality of a cohort of eyes with normal visual acuity is represented by a numerical number including a percentiles by ranking the calculated MTF of the tested eye against MTFs of a cohort of eyes with normal acuity.

31. The method of claim 28, wherein the calculated image quality parameter is a Strehl Ratio, or a volume under a 2 dimension MTF of the eye up to a spatial frequency about 60 cycle/deg.

32. The method of claim 28, further includes specification of quality of a correction lens in a plurality of pupil sizes.

* * * * *